United States Patent [19]

Björnson

[11] 4,258,268

[45] Mar. 24, 1981

[54] POLYCYCLIC PHENOLS, ALCOHOLS AND KETONES FROM PHENOLS, CYCLIC ALCOHOLS AND CYCLIC KETONES USING A NICKEL OXIDE/MANGANESE OXIDE/MAGNESIUM OXIDE CATALYST IN PRESENCE OF AT LEAST ONE OF HYDROGEN AND NITROGEN

[75] Inventor: Geir Björnson, Bartlesville, Okla.

[73] Assignee: Phillips Petroleum Company, Bartlesville, Okla.

[21] Appl. No.: 69,966

[22] Filed: Aug. 27, 1979

[51] Int. Cl.$^3$ ................... C07C 27/06; C07C 29/132

[52] U.S. Cl. ................... 568/350; 568/743; 568/747; 568/799; 568/816; 568/835; 568/361; 568/362; 568/367

[58] Field of Search ............... 568/731, 743, 816, 799, 568/715, 747, 835; 260/586 P

[56] References Cited

U.S. PATENT DOCUMENTS

| 2,396,013 | 3/1946 | Jones et al. | 568/743 |
|---|---|---|---|
| 2,819,995 | 1/1958 | Wassell | 568/743 |
| 3,124,614 | 3/1964 | Dankert et al. | 260/586 C |
| 3,213,037 | 10/1965 | Hodgkiss | 252/450 |
| 3,256,334 | 6/1966 | Scheidt | 260/586 C |
| 3,316,303 | 4/1967 | Mertziviller et al. | 260/586 C |
| 3,367,981 | 2/1968 | Napolitano | 568/790 |
| 3,418,379 | 12/1968 | Parsey et al. | 568/790 |
| 3,766,275 | 10/1973 | Ciaudelli | 260/609 R |
| 3,829,495 | 8/1974 | Mizitant et al. | 260/586 C |
| 3,873,638 | 3/1975 | Van Sorge | 568/743 |
| 3,980,716 | 9/1976 | Elliott | 260/586 C |
| 4,002,693 | 1/1977 | Kings et al. | 260/586 C |

OTHER PUBLICATIONS

Blagdeu et al., Chem. Abst., vol. 28, #1060$^2$ (1933).
Backer et al., Chem. Abst., vol. 38, #89$^8$ (1942).

*Primary Examiner*—James H. Reamer

[57] ABSTRACT

At least one of a polycyclic phenol, a polycyclic alcohol and a polycyclic ketone is produced under hydrogenation conditions using a nickel oxide/manganese oxide/magnesium oxide catalyst by subjecting at least one of a monocyclic ketone, a monocyclic alcohol and a monocyclic phenol to said conditions and said catalyst.

21 Claims, No Drawings

POLYCYCLIC PHENOLS, ALCOHOLS AND KETONES FROM PHENOLS, CYCLIC ALCOHOLS AND CYCLIC KETONES USING A NICKEL OXIDE/MANGANESE OXIDE/MAGNESIUM OXIDE CATALYST IN PRESENCE OF AT LEAST ONE OF HYDROGEN AND NITROGEN

BRIEF SUMMARY OF THE INVENTION

Various phenols, cyclic alcohols and cyclic ketones are converted to polycyclic phenols, polycyclic alcohols and polycyclic ketones under hydrogenation conditions in presence of a nickel oxide/manganese oxide/magnesium oxide catalyst. A range of reaction products are obtained. Nitrogen alone or in combination with hydrogen can be used similarly to obtain such products.

DETAILED DESCRIPTION

This invention relates to the production of at least one of a polycyclic phenol, polycyclic alcohol and a polycyclic ketone. In one of its aspects the invention relates to a process for producing such compounds by hydrogenation. In another of its aspects the invention relates to a hydrogenation process for producing such compounds using a catalyst.

In one of its concepts the invention provides a process for the production of at least one polycyclic phenol, polycylcic ketone and a polycyclic alcohol which comprises subjecting, under hydrogenation conditions, at least one of a phenol, a monocyclic alcohol, and a monocyclic ketone to the action of a catalyst consisting essentially of oxides of nickel, manganese and magnesium. In a more specific concept the invention provides a process for the conversion of at least one of phenol, cyclohexanol, and cyclohexanone to at least one polycyclic phenol, polycyclic ketone and polycyclic alcohol by subjecting the same hydrogenation conditions at an elevated hydrogen pressure to the action of a catalyst consisting essentially of nickel oxide/manganese oxide/magnesium oxide. In a further concept of the invention it provides a process for the hydrogenation of compounds as herein described wherein a so called short-stop aldol condensation type reaction is effected employing conditions and catalysts as herein described. In another concept nitrogen alone or together with hydrogen is used.

Polycyclic phenols, alcohols and ketones have usefulness in a wide variety of application areas ranging from antioxidants in gasoline and plastics to ingredients in perfumes, insect repellants, plasticizers, rubber lubricants, etc. Generally, these polycyclic materials are prepared as a single product from a single reaction. For example, U.S. Pat. No. 3,766,276 describes the synthesis of 2-cyclohexylphenol from the reaction of phenol and cyclohexane in the presence of an aluminum phenoxide catalyst. U.S. Pat. No. 3,124,614 discloses the hydrogenation of 2-cyclohexylphenol to 2-cyclohexylcyclohexanone using a palladium catalyst. Chemical Abstracts 36: 89[8] reports that cyclohexanone is reduced with magnesium metal, mercuric chloride and alumina to give some 2,6-dicyclohexylcyclohexanone. Finally, Chemical Abstracts 28: P1060[1] describes the hydrogenation of cyclohexylidenecyclohexanone to cyclohexylcyclohexanol using a non-noble metal catalyst such as Fe, Ni, or Cu. The catalyst may contain a promotor, e.g., MgO, $Co_2O_3$.

All of the above examples provide primarily only the one product and in some cases from reactants that are expensive when used as isolated or purified reactants.

It would be convenient and therefore desirable to make some of the above products from a single and relatively inexpensive reactant such as phenol or cyclohexanone. It would be even more advantageous and therefore desirable if several of the above polycyclic products could be made in a single step reaction from a single reactant and in a continuous process. These latter features are, in part, some of the features of the current invention.

It is an object of this invention to produce at least one of a polycyclic phenol, polycyclic alcohol, and a polycyclic ketone. It is another object of this invention to convert at least one of a phenol, a monocyclic alcohol, and a monocyclic ketone to a range of products including a polycyclic phenol, a polycyclic alcohol, and a polycyclic ketone. It is a further object of the invention to provide a hydrogenation process employing a catalyst under conditions to produce a range of products as herein described from starting materials as also herein described. It is further object of the invention to convert cyclohexanol to a range of products including a polycyclic phenol, a polycyclic alcohol and a polycyclic ketone.

Other aspects, concepts, objects and the several advantages of the invention are apparent from a study of this disclosure and the appended claims.

According to the present invention there is provided a process for the production of at least one of a polycyclic phenol, a polycyclic hetone and a polycyclic alcohol which comprises subjecting under hydrogenation conditions at least one of a phenol, a monocyclic ketone and a monocyclic alcohol to the action of a catalyst consisting essentially of oxides of nickel, manganese and magnesium.

Also according to the present invention there is provided a process as herein described wherein the distribution of products obtained can be made to be different depending upon the hydrogenation pressure.

Further, according to the present invention the product distribution can be made to vary depending upon the ratio of hydrogen to the material being converted.

The monocyclic materials useful as feedstock in this invention can be any compound having at least one alpha hydrogen atom attached to a ring carbon atom which is adjacent to a ring carbon atom having an oxygen atom such as hydroxyl group or ketone. These type compounds are represented by any of the general formulas

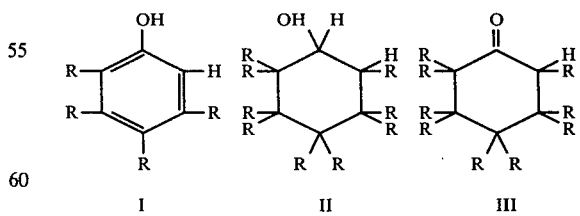

wherein R can be hydrogen, an alkyl or cycloalkyl radical having from 1 to 6 carbon atoms. For example, materials to be used that correspond to Formula I can be, but are not limited to:
phenol
o-cresol m-cresol
p-cresol
2,3-xylenol
2,4-xylenol
2,5-xylenol
3,4-xylenol
3,5-xylenol
2,3,4-trimethylphenol
2,3,5-trimethylphenol
3,4,5-trimethylphenol
2-ethylphenol
2-hexylphenol
2,4-dihexylphenol
2-methyl-4-ethylphenol
2-cyclohexylphenol
and the like, and mixtures thereof. Materials to be used that correspond to formula II can be, but are not limited to:
cyclohexanol
2-methylcyclohexanol
3-methylcyclohexanol
4-methylcyclohexanol
2,3-dimethylcyclohexanol
2,4-dimethylcyclohexanol
2,5-dimethylcyclohexanol
3,4-dimethylcyclohexanol
3,5-dimethylcyclohexanol
2,3,4-trimethylcyclohexanol
2,3,5-trimethylcyclohexanol
3,4,5-trimethylcyclohexanol
2-ethylcyclohexanol
2-hexylcyclohexanol
2,4-dihexylcyclohexanol
2-methyl-4-ethylcyclohexanol
2-cyclohexylcyclohexanol
and the like, and mixtures thereof. Materials to be used that correspond to formula III can be, but are not limited to:
cyclohexanone
2-methylcyclohexanone
3-methylcyclohexanone
4-methylcyclohexanone
2,3-dimethylcyclohexanone
2,4-dimethylcyclohexanone
2,5-dimethylcyclohexanone
3,4-dimethylcyclohexanone
3,5-dimethylcyclohexanone
2,3,4-trimethylcyclohexanone
2,3,5-trimethylcyclohexanone
3,4,5-trimethylcyclohexanone
2-ethylcyclohexanone
2-hexylcyclohexanone
2,4-dihexylcyclohexanone
2-methyl-4-ethylcyclohexanone
2-cyclohexylcyclohexanol
and the like and mixtures thereof.

It is within the scope of the invention and the claims thereto to have present initially or as the reaction proceeds more than one of the compounds for which formulas have been given above, including compounds names of which have been given above.

The method of preparing the catalyst useful in this invention is not a critical feature and any known method can be used. The essential elements manganese oxide and nickel oxide of the catalyst, for example, can be deposited on a support such as magnesium oxide by impregnation with an aqueous solution of manganese nitrate or nickel nitrate or both. Alumina can be present with the magnesium oxide but is not essential. The nickel oxide/manganese oxide/magnesium oxide catalyst is somewhat brittle with little cohesive strength. The cohesive strength can be increased by use of a binder. Such a binder can be a blend of fumed silica (Cab-O-Sil®) and water glass (sodium silicate plus water). The hydrated catalyst is dried, preferably under vacuum followed by calcining with air or nitrogen or mixtures thereof at 204° C. followed by a subsequent heating at about 400° C. for 30 minutes in the presence of hydrogen. Hydrogen reduces the metal oxide to its lowest possible valence state while still an oxide. The hydrogen pretreatment also helps to maintain catalyst composition consistency before the feed is introduced. The initial heating or activation of these nitrate type catalysts should be done outside the reactor because of the nitrous and nitric acid by-products formed during heating that can be harmful to the metal reactor or metal packing. Thereafter, the catalyst can be regenerated in the tubular reactor by passing nitrogen, air, or mixtures thereof over the catalyst at about 200° C. to about 400° C. The amount of manganese oxide present expressed as free maganese can be broadly 5 to 30 wt. percent of the total catalyst system but is is preferred to be about 10 to 25 wt. percent.

The amount of nickel oxide present expressed as free nickel can be broadly from about 2 to 25 wt. percent of the total catalyst system but it is preferred to be about 5 to 20 wt. percent. The wt. ratio of nickel oxide to manganese oxide expressed as free metal can be broadly 0.5:1 to 3:1 but the preferred ratio is about 2:1.

The magnesium oxide employed can be as a pellet to which the aqueous nitrate solutions are mixed and heated or in the form of a water insoluble hydroxide which is subsequently decomposed to magnesium oxide. If pelleted or granulated magnesium oxide is employed it is preferred that the particle size be less than 50 mesh as measured by a U.S. Standard sieve screen although any convenient size can be used. The amount of magnesium oxide present expressed as free metal can be broadly 50 to 90 wt. percent of the total catalyst system but it is preferred to be about 60 to 80 wt. percent.

Aluminum oxide is optionally used in the catalyst system as a nickel oxide activator which is known in the art. The amount of aluminum oxide used is generally less than about 2 wt. percent of the total catalyst system and preferably from 0.1 to 1.0 wt. percent.

The catalyst system employed in the present invention has been disclosed and claimed elsewhere.

The amount of hydrogen used is expressed as a mole ratio of hydrogen to reactant feed (undiluted) and can be broadly from 1:1 to 20:1 but preferably from 1:1 to about 10:1. The amount of hydrogen used depends upon the desired products. For example, the more hydrogen used (or the higher the hydrogen to feed mole ratio) the more ring saturated products are formed. Hydrogen can be diluted with inert gases such as nitrogen.

The use of solvents in this invention is optional. The amount of solvent used can be about 25 to 75 wt. percent of the total feed. Solvents useful are the alkanes and cycloalkanes having from about 5 to 7 carbon atoms such as pentane, hexane, heptane, methylcyclopentane, cyclohexane, and the like.

The following are the now preferred conditions for the reactions of the invention, as described.

|  | Broad | Preferred |
|---|---|---|
| 1. Temperature |  |  |
| °F. | 250–750 | 400–600 |
| °C. | 121–399 | 204–316 |
| 2. Pressure |  |  |
| psig | 0–1000 | 100–700 |
| MPa | 0–6.89 | 0.689–4.82 |
| 3. Flow Rates |  |  |
| Liquid Hourly Space Velocity (LHSV) | 0.1–10 | 0.5–5.0 |

The following equations illustrate the reactions now thought to occur in the process of the present invention when at least one of phenol, cyclohexanol and cyclohexanone is present as starting material.

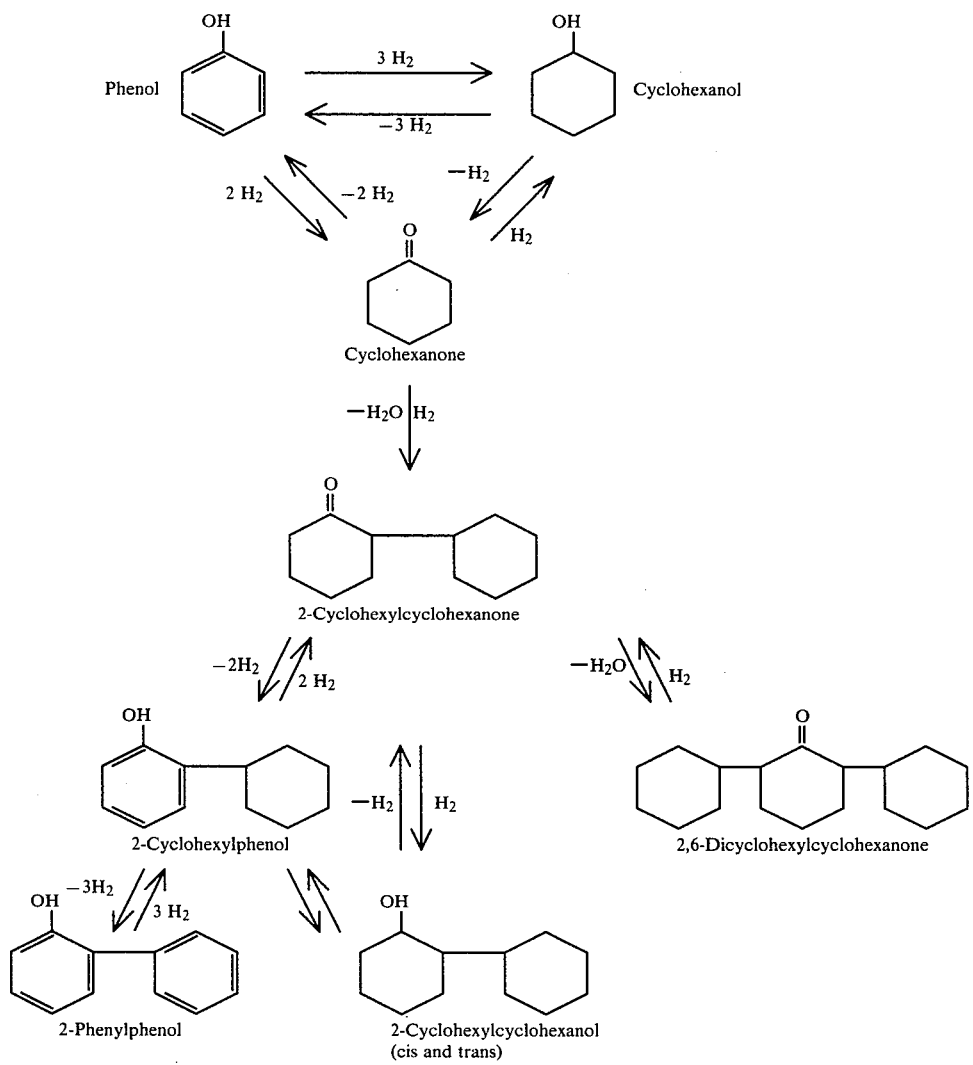

The following examples illustrate the invention.

Example I

Preparation of Catalyst

A preparation of the catalyst used in this invention was carried out as follows. To 90 milliliters of a solution containing 1.8 grams $Al(NO_3)_3.9\ H_2O$, 33.0 grams $Ni(NO_3)_2.6\ H_2O$, 11.7 grams $Mn(NO_3)_2$, and 60 grams of $H_2O$ was added 59.1 grams $Mg(OH)_2$, 0.5 grams fumed $SiO_2$ (Cab-O-Sil ®), and 6 milliliters of water glass (2 grams $NaSiO_3.9\ H_2O$). The soupy mixture was stirred for several minutes and allowed to stand overnight at ambient room temperature. The mix was again stirred and cast into a 15.24 cm. (6 in.)×0.32 cm. (0.125 in.)×0.32 cm. (0.125 in.) rubber mold. After drying at ambient room temperature overnight, the mold and catalyst were placed in a vacuum over (20 mm) at 93° F.) for two hours. The slab of catalyst which formed was broken into small pieces and calcined in a quartz or glass tube with a 50:50 volume percent air and nitrogen passing through the catalyst, first at 316° C.-371° C. (600° F.-700° F.) to remove oxides of nitrogen, then at 482° C. (900° F.-950° F.). An alternate method of removing water and nitrogen oxides is to put the catalyst in a vacuum oven (<10 mm pressure) for 16–24 hours at 204° C. (400° F.). Catalyst dried by either method is activated by heating to about 10° C. (50° F.) above the desired operating temperature while a stream of hydrogen, comprised of some nitrogen initially, is passed through the reactor tube containing the catalyst. The ratio of the active nickel to manganese catalyst ingredients at this point is estimated as shown in Table I. Since the exact oxide form of the metal is not known, the values are expressed on the basis of free metal.

| Metal Ingredient | Proportions of Metals | | |
|---|---|---|---|
| | Molar Ratio[a] | Wt. Ratio[a] | Wt. % |
| Manganese | 1.0 | 1.0 | 10.2 |
| Nickel | 1.7 | 1.86 | 18.8 |
| Magnesium | 15.5 | 6.86 | 69.7 |
| Aluminum | 0.06 | 0.03 | 0.3 |

[a]Based on 1.0 for manganese

Example II

Conversion of Cyclohexanone

The following is a typical example illustrating the current invention. To a 316 stainless steel tubular reactor having the dimensions 2.44 cm. (0.960 in.) diameter by 70.49 cm. (27.75 in.) and equipped with an external electrical heater and a Moore back-pressure regulator was charged 60 milliliters of the catalyst system described in Example I mixed with about 73 milliliters of 316 stainless steel (0.125 in.×0.125 in.) Helipak which was used as a heat transfer agent to help control the temperature of the reaction which was usually exothermic. While the temperature was maintained at about 316° C. (600° F.) and the pressure at about 200 psi (2.91 MPa), a 50–50 by weight mixture of cyclohexanone-cyclohexane was fed through the reactor at a rate of about 80 milliliters per hour (1.33 LHSV), the pressure being maintained by hydrogen which mixes with the feed at molar ratio of about 1 mole of hydrogen to 1 mole of cyclohexanone. The effluent product was analyzed without further separation with a Bendix ® 2300 chromatograph employing a column packed with a polyethylene glycol, mol wt. 20,000 (Carbowax ® 20M from Union Carbide). The column was programmed as follows: 100° C. to 190° C. at 30° C./min.; 190° C. to 250° C. at 10°C./min.; and isothermal at 250° C. until complete. The analysis showed a 73.4% conversion of cyclohexanone with the following % selectivity:

| | |
|---|---|
| 13.8% | cyclohexanol |
| 24.6% | phenol |
| 27.3% | 2-cyclohexylphenol |
| 25.5% | 2-cyclohexylcyclohexanone |
| 4.4% | 2-cyclohexylcyclohexanol (cis and trans) |
| 3.0% | 2-phenylphenol |

This example shows that when the cyclohexanone and the hydrogen are each of them present in a substantial amount there are formed a range of products, as earlier described.

Example III

The effect of H$_2$ pressure on the product distribution of the current invention was studied as follows. The process described in Example II was repeated except the H$_2$ pressure was varied from 0 to 600 psi (4.14 MPa). These results, which are listed in Table II along with those described in Example II for comparison, show that as the pressure is increased the amount of higher molecular weight products is increased, such as those with ring saturation and those having 2 and 3 ring structures.

TABLE II

Effect of Hydrogen Pressure on Product Distribution at a Ratio of 1 Mole H$_2$: 1 Mole Cyclohexanone

| Products | O | % Selectivity at Various H$_2$ Pressures | | | |
|---|---|---|---|---|---|
| | | 50 psig | 200 psig | 400 psig | 600 psig |
| Cyclohexanol | 2.9 | 7.5 | 13.8 | 24.8 | 27.2 |
| Phenol | 61.8 | 49.2 | 24.6 | 5.5 | — |
| 2-Cyclohexylphenol | 21.3 | 25.2 | 27.3 | 16.2 | 8.1 |
| 2-Cyclohexylcyclohexanone | 2.5 | 10.6 | 25.5 | 37.7 | 32.2 |
| 2-Cyclohexylcyclohexanol (cis & trans) | — | — | 4.4 | 13.0 | 19.7 |
| 2-Phenylphenol | 11.1 | 6.8 | 3.0 | — | — |
| 2,6-Dicyclohexylcyclohexanone | — | — | — | — | 8.4 |
| % Cyclohexanone conversion | 70.3 | 50.4 | 73.4 | 80.0 | 87.8 |

Table II show that the cyclohexanone conversion is increased with increased hydrogen pressure.

The run reported in the first column of Table II contained no hydrogen. A pressure of 50 psig nitrogen was used. Comparison of this column and the second column shows the effect of the hydrogen on product distribution. The "O" in Column 1 indicates absence of added hydrogen.

Table II shows that cyclohexanone conversion increased with increase in hydrogen pressure; also that the product distribution obtained was substantially varied. Accordingly the invention provides a process for maximizing one reaction product with respect to another.

Example IV

This example illustrates the effect on product distribution when the mole ratio of hydrogen to cyclohexanone is increased from 1:1 (Example III) to 3:1. These results, which are listed in Table III, when compared with those in Example III show that the higher H$_2$:cyclohexanone ratio of 3:1 generally favors higher cyclohexanone conversions and increased amounts of higher molecular weight products, particularly those having 2 and 3 saturated ring structures. At the same time, the higher mol ratios suppress the formation of phenol.

TABLE III

Effect of Hydrogen Pressure on Product Distribution at a Ratio of 3 Moles H$_2$: 1 Mole Cyclohexanone

| Products | % Selectivity at Various Pressures | | |
|---|---|---|---|
| | 50 psig | 200 psig | 400 psig |
| Cyclohexanol | 17.2 | 28.8 | 39.0 |
| Phenol | 17.0 | — | — |
| 2-Cyclohexylphenol | 24.3 | 2.9 | — |
| 2-Cyclohexylcyclohexanone | 48.4 | 40.2 | 24.9 |
| 2-Cyclohexylcyclohexanol (cis & trans) | 2.7 | 16.7 | 23.4 |
| 2-Phenylphenol | — | — | — |
| 2,6-Dicylohexylcyclohexanone | — | 11.1 | 12.0 |
| % Cyclohexanone conversion | 36.7 | 75.7 | 85.9 |

Tables II and III, considered together, indicate the flexibility with which product distribution as may be desired can be effected within reasonable ranges.

It is thought the products herein described are obtained by a "short-stop aldol condensation" mechanism. By "short-stopping aldol condensation" is meant that only a limited number of molecules (e.g. 2 or 3) react or are condensed probably because of short residence times, catalyst specificity, etc. Ordinarily, complete aldol condensations result in multiplicity of molecules reacting to generally form polymeric products.

Reasonable variation and modification are possible within the scope of the foregoing disclosure and the claims to the invention the essence of which is that at least one of polycyclic phenol, a polycyclic ketone and a polycyclic alcohol can be produced by subjecting under hydrogenation conditions at least one of amonocyclic ketone, a monocyclic alcohol and a monocyclic phenol to the action of a catalyst consisting essentially of oxides of nickel, manganese and magnesium, as described, wherein hydrogen can be replaced at least in part with nitrogen.

We claim:

1. A process for the production of at least one of a polycyclic phenol, a polycyclic ketone, and a polycyclic alcohol, which comprises subjecting under hydrogenation conditions at least one of a monocyclic ketone, a monocyclic alcohol and a monocyclic phenol to the action of a catalyst consisting essentially of oxides of nickel, manganese and magnesium wherein the compounds involved can be represented by the formulas

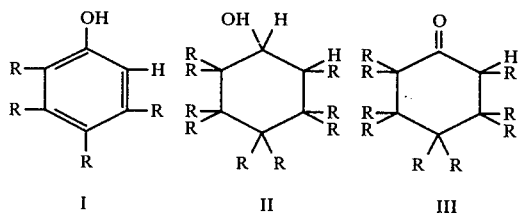

wherein R can be one of hydrogen, an alkyl radical and a cycloalkyl radical each having from 1 to 6 carbon atoms, inclusive.

2. A process according to claim 1 wherein the compound is at least one selected from
phenol
o-cresol
m-cresol
p-cresol
2,3-xylenol
2,4-xylenol
2,5-xylenol
3,4-xylenol
3,5-xylenol
2,3,4-trimethylphenol
2,3,5-trimethylphenol
3,4,5-trimethylphenol
2-ethylphenol
2-hexylphenol
2,4-dihexylphenol
2-methyl-4-ethylphenol
2-cyclohexylphenol
cyclohexanol
2-methylcyclohexanol
3-methylcyclohexanol
4-methylcyclohexanol
2,3-dimethylcyclohexanol
2,4-dimethylcyclohexanol
2,5-dimethylcyclohexanol
3,4-dimethylcyclohexanol
3,5-dimethylcyclohexanol
2,3,4-trimethylcyclohexanol
2,3,5-trimethylcyclohexanol
3,4,5-trimethylcyclohexanol
2-ethylcyclohexanol
2-hexylcyclohexanol
2,4-dihexylcyclohexanol
2-methyl-4-ethylcyclohexanol
2-cyclohexylcyclohexanol
cyclohexanone
2-methylcyclohexanone
3-methylcyclohexanone
4-methylcyclohexanone
2,3-dimethylcyclohexanone
2,4-dimethylcyclohexanone
2,5-dimethylcyclohexanone
3,4-dimethylcyclohexanone
3,5-dimethylcyclohexanone
2,3,4-trimethylcyclohexanone
2,3,5-trimethylcyclohexanone
3,4,5-trimethylcyclohexanone
2-ethylcyclohexanone
2-hexylcyclohexanone
2,4-dihexylcyclohexanone
2-methyl-4-ethylcyclohexanone
2-cyclohexylcyclohexanol 3. A process according to claim 1 wherein the catalyst contains the oxides, expressed as a free metal, in approximate weights percent, respectively, as follows: 2 to 25; 5 to 30; and 50 to 90.

4. A process according to claim 1 wherein the catalyst contains the oxides, expressed as a free metal, in approximate weights percent, respectively, as follows: 5 to 20; 10 to 25; and 60 to 80.

5. A process according to claim 2 wherein the catalyst contains the oxides, expressed as a free metal, in approximate weights percent, respectively, as follows: 2 to 25; 5 to 30; and 50 to 90.

6. A process according to claim 2 wherein the catalyst contains the oxides, expressed as a free metal, in approximate weights percent, respectively, as follows: 5 to 20; 10 to 25; and 60 to 80.

7. A process according to claim 1 wherein the weight ratio of the nickel oxide to manganese oxide, expressed as the free metal is in the approximate range of from about 0.5:1 to about 3:1.

8. A process according to claim 1 wherein the weight ratio of the nickel oxide to manganese oxide, expressed as the free metal is approximately 2:1.

9. A process according to claim 2 wherein the weight ratio of the nickel oxide to manganese oxide, expressed as the free metal is in the approximate range of from about 0.5:1 to about 3:1.

10. A process according to claim 2 wherein the weight ratio of the nickel oxide to manganese oxide, express as the free metal is approximately 2:1.

11. A process according to claim 1 wherein the hydrogen pressure is substantially elevated.

12. A process according to claim 11 wherein the hydrogen pressure is at least about 50 psi.

13. A process according to claim 11 wherein the hydrogen pressure is at least about 100 psi.

14. A process according to claim 3 wherein the hydrogen pressure is at least about 50 psi.

15. A process according to claim 2 wherein the hydrogen pressure is at least about 100 psi.

16. A process according to claim 1 wherein cyclohexanone is converted to a mixture containing cyclohexanol, phenol, 2-cyclohexylphenol, 2-cyclohexylcyclohexanone, 2-cyclohexylcyclohexanol, and 2-phenylphenol, and 2,6-dicyclohexylcyclohexanone.

17. A process according to claim 16 wherein the hydrogen pressure is maintained at a substantially elevated value.

18. A process according to claim 16 wherein the ratio of hydrogen to cyclohexanone is maintained substantially above about 1.

19. A process according to claim 16 wherein the hydrogen pressure is at least about 100 psi.

20. A process according to claim 1 wherein an appreciable proportion of nitrogen is present during the production.

21. A process for the production of at least one of a polycyclic phenol, a polycyclic ketone, and a polycyclic alcohol, which comprises subjecting to an elevated temperature in the presence of nitrogen at least one of a monocyclic ketone, a monocyclic alcohol, and a monocyclic phenol to the action of a catalyst consisting essentially of oxides of nickel, manganese and magnesium wherein the compounds involved can be represented by the formulas

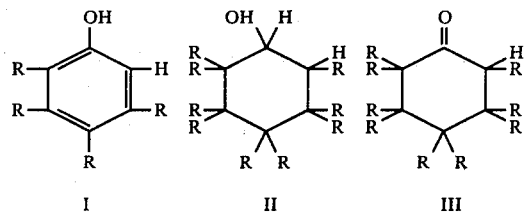

wherein R can be one of hydrogen, an alkyl radical and a cycloalkyl radical each having from 1 to 6 carbon atoms, inclusive.

* * * * *